United States Patent
Schoonover (10) Patent No.: US 9,568,390 B2
(45) Date of Patent: Feb. 14, 2017

(54) SYSTEM AND METHOD FOR FILTERING NOISE FROM ACOUSTIC ENERGY FROM A VALVE

(71) Applicant: Dresser Inc., Addison, TX (US)

(72) Inventor: Larry Gene Schoonover, Falmouth, MA (US)

(73) Assignee: Dresser, Inc., Addison, TX (US)

( * ) Notice: Subject to any disclaimer, the term of this patent is extended or adjusted under 35 U.S.C. 154(b) by 751 days.

(21) Appl. No.: 13/928,991

(22) Filed: Jun. 27, 2013

(65) Prior Publication Data

US 2015/0006091 A1    Jan. 1, 2015

(51) Int. Cl.

| | |
|---|---|
| G01B 5/30 | (2006.01) |
| G01M 3/00 | (2006.01) |
| G01N 29/44 | (2006.01) |
| F16K 37/00 | (2006.01) |
| G05B 9/02 | (2006.01) |
| G01N 29/14 | (2006.01) |
| G01N 29/46 | (2006.01) |

(52) U.S. Cl.
CPC .............. *G01M 3/007* (2013.01); *F16K 37/00* (2013.01); *G01N 29/14* (2013.01); *G01N 29/4454* (2013.01); *G01N 29/46* (2013.01); *G05B 9/02* (2013.01)

(58) Field of Classification Search
CPC ............................... G01M 3/007; F16K 37/00
USPC .............................................. 702/39, 48, 45
See application file for complete search history.

(56) References Cited

U.S. PATENT DOCUMENTS

| | | |
|---|---|---|
| 4,543,817 A | 10/1985 | Sugiyama |
| 4,785,659 A | 11/1988 | Rose et al. |
| 4,958,296 A | 9/1990 | Saitoh et al. |
| 5,136,876 A | 8/1992 | Taylor |
| 5,231,866 A | 8/1993 | Peacock |
| 5,361,636 A | 11/1994 | Farstad et al. |
| 5,955,670 A | 9/1999 | Goodman et al. |
| 5,974,862 A | 11/1999 | Lander et al. |
| 6,134,949 A | 10/2000 | Leon et al. |
| 6,668,619 B2 | 12/2003 | Yang et al. |
| 6,725,705 B1 | 4/2004 | Huebler et al. |
| 6,857,308 B2 | 2/2005 | Johnson et al. |
| 2002/0124633 A1* | 9/2002 | Yang ................. G01M 3/243 73/40.5 R |

(Continued)

OTHER PUBLICATIONS

Yang et al. "Cavitation detection of butterfly valve using support vector machines", Journal of Sound & Vibration, London, GB, vol. 287, No. 1-2, pp. 25-43, Oct. 6, 2005 XP004979420.

(Continued)

*Primary Examiner* — Gregory J Toatley
*Assistant Examiner* — Eman Alkafawi
(74) *Attorney, Agent, or Firm* — Paul Frank + Collins P.C.

(57) ABSTRACT

Embodiments of systems and methods that can filter acoustic energy from sources remote from the valve. These embodiments utilize signals from sensors that manifest acoustic energy from various locations on and/or about the valves. In one embodiment, the system includes sensors at locations proximate the valve and locations spaced apart from the valve. The system can further process the signals from these locations and, in one example, combines samples of data to form an energy signature of the valve that is effectively free of noise that emanates from upstream and/or downstream of the valve.

20 Claims, 7 Drawing Sheets

(56) References Cited

U.S. PATENT DOCUMENTS

| | | | | |
|---|---|---|---|---|
| 2006/0174707 A1* | 8/2006 | Zhang | .................. | G01M 3/243 |
| | | | | 73/592 |
| 2010/0190075 A1* | 7/2010 | Frost | ................. | H01M 8/04231 |
| | | | | 429/433 |
| 2011/0161037 A1* | 6/2011 | Sutherland | .............. | F16L 55/48 |
| | | | | 702/103 |
| 2013/0283919 A1* | 10/2013 | Coonrod | ............. | E21B 33/0355 |
| | | | | 73/632 |
| 2014/0114551 A1* | 4/2014 | Mac Ewen | ............. | F02D 41/22 |
| | | | | 701/102 |

OTHER PUBLICATIONS

PCT Search Report and Written Opinion issued in connection with corresponding Application No. PCT/US2014/042833 on Oct. 16, 2014.

* cited by examiner

SYSTEM AND METHOD FOR FILTERING NOISE FROM ACOUSTIC ENERGY FROM A VALVE

BACKGROUND

The subject matter disclosed herein relates to signal processing and, in one or more embodiments, to systems and methods to remove and/or filter acoustic energy from signals that monitor operation of valves in a process facility.

Valves in process facilities can exhibit various types of failure modes that can result in serious economic consequences and can pose a safety risk. Cavitation is one failure mode that occurs when the pressure drop across the valve causes the pressure of the working fluid to drop below the vapor pressure. This pressure drop causes gas bubbles to form. Collapse of these bubbles can damage the valve and piping. In another mode, the valve fails to close completely, which causes the working fluid to leak through the valve. Such leaks can indicate numerous problems with the valve. These problems may include damage to the components (e.g., the plug and/or the stem), the presence of debris that blocks and/or prevents full actuation of the plug, as well as failure of the actuator to provide enough force to fully close the valve.

Process facilities may employ several methods to detect these failure modes, as well as other problems with the valves. Examples of these methods often look for deviations in flow or pressure, e.g., downstream (and/or upstream) of the valve. In another example, the method monitors noise emitted by the valve. These methods are particularly useful because some mechanical failures (e.g., in the stem, the plug, the seat, and/or the valve actuator) may cause vibrations. Valves that are nearly closed often emit vibrations that indicate the presence of a leak in the valve. Detecting the acoustic energy of these vibrations and comparing the acoustic energy to the spectra of known leaking valves can help to detect the presence of leaks.

Although acoustic methods can detect leakage in pipelines, these methods are difficult to apply in a process plant because the valves in the process plant are subject to many acoustic sources that can interfere with the technique. Some methods overcome the problem with interference by restricting the detected frequency to the ultrasonic range. These frequencies are less influenced by energy that emanates from acoustic sources that are distant from the valve. Other methods measure ambient acoustic noise and directly subtract this measure from the signal that measures the acoustic energy at the valve. However, this method does not eliminate noise that can occur along the pipe. To further address the noise along the pipe, other methods have utilized multiple acoustic sensors; but, these methods have used the arrival times of the acoustic energy at the sensors to locate the "position" of the acoustic source in space rather than for the elimination of noise at the event.

BRIEF DESCRIPTION OF THE INVENTION

This disclosure describes embodiments of systems and methods that can filter acoustic energy from sources remote from the valve. These embodiments utilize signals from sensors that manifest acoustic energy from various locations on and/or about the valves. In one embodiment, the system includes sensors at locations proximate the valve and locations spaced apart from the valve. The system can further process the signals from these locations and, in one example, combine samples of data to form an energy signature of the valve that is effectively free of noise that emanates from upstream and/or downstream of the valve.

BRIEF DESCRIPTION OF THE DRAWINGS

Reference is now made briefly to the accompanying drawings, in which.

Where applicable like reference characters designate identical or corresponding components and units throughout the several views, which are not to scale unless otherwise indicated.

DETAILED DESCRIPTION

Figure 1:
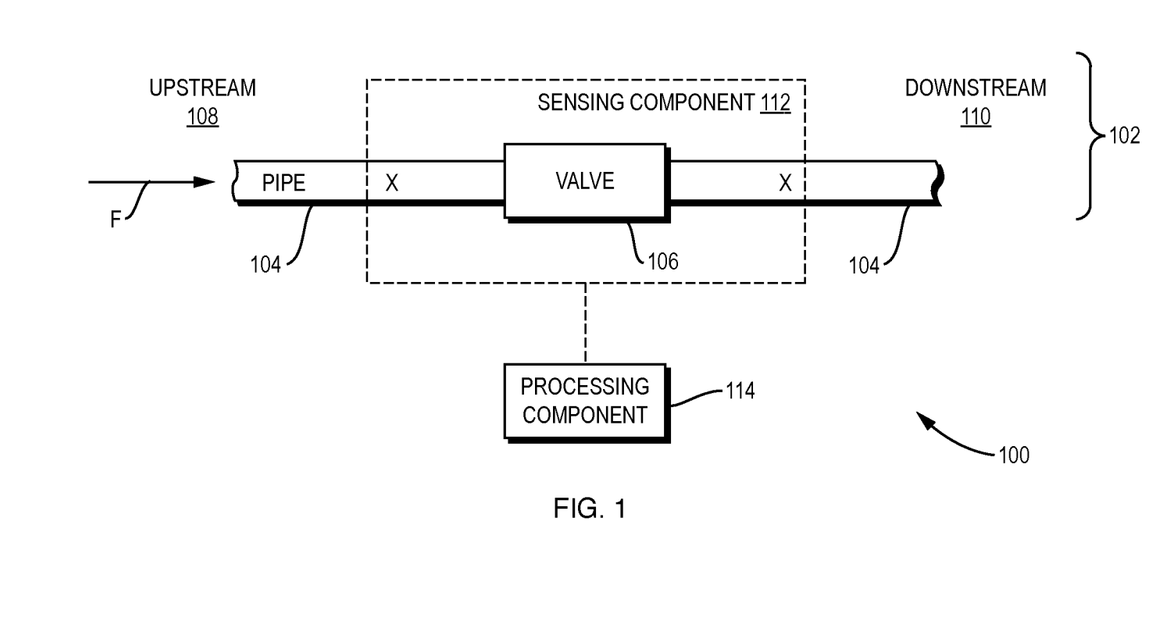
FIG. 1 depicts a schematic diagram of an exemplary embodiment of a system to monitor acoustic energy at a valve in a portion of a process facility.

FIG. 1 depicts a schematic diagram of an exemplary embodiment of a system 100 that can monitor conditions at components found in a process facility. The illustration of FIG. 1 represents a portion 102 of the process facility. The portion 102 includes one or more pipes 104 and a valve 106. Operation of the valve 106 regulates flow of a working fluid F from an upstream side 108 to a downstream side 110 of the portion 102. The system 100 includes a sensor component 112 and a processing component 114 that exchanges signals with the sensor component 112. Examples of the processing component 114 can generate an output with data that is useful to understand operation of the valve 106. Further processing of this data can detect operating conditions of the valve 106 that may result in damage to the valve 106 and/or that may lead to injury of individuals in the vicinity of the valve 106.

Examples of the system 100 address problems that arise from propagation of noise within the portion 102. This noise can distort signals that the sensor component 112 collects from the valve 106. Noise can frustrate diagnosis of problematic operating conditions of the valve 106. As discussed more below, the processing component 114 can filter out noise that arises from points remote (also, "distant") from the valve 106, e.g., at one or more of the upstream side 108 and the downstream side 110. This feature removes the influence of noise from the data of the output that may result from disturbances remote from the valve 106.

Broadly, the sensor component 112 can include devices that are sensitive to operating conditions at the valve 106 and/or within the portion 102 of the processing facility. Examples of these devices can include accelerometers and pressure sensors. These devices can generate signals, e.g., in response to acoustic waves that propagate through a medium. In one example, the medium may include one or more of the pipes 104, the valve 106, and the working fluid F.

Configurations of the processing component 114 can include circuitry that is useful to process the signals. This circuitry can include analog and digital components. The latter components, i.e., the digital components, may utilize one or more processors, memory, and like discrete elements. This type of digital circuitry can execute instructions (also "executable instructions") that define the steps to process the signals and, in one example, generate the output that is effectively free of noise from parts remote from the valve 106.

Implementation of the sensor component 112 and the processing component 114 recognizes that acoustic waves can arise from the valve 106 and from elsewhere, e.g., along the pipes 104 on the upstream side 108 and the downstream side 110 of the valve 106. These waves can propagate in different directions, ultimately influencing the data of the signals at the sensors 106 found throughout the portion 102 of the process facility. For example, waves from the valve 106 can propagate to the upstream side 108 and the downstream side 110. Waves that occur on the upstream side 308 can propagate across the valve 106 to the downstream side 110, and vice versa.

During one exemplary operation, the sensor component 112 can generate signals with data that manifests both the acoustic energy from the valve 106 and the acoustic energy from one or more locations that are remote from the valve 106. This configuration can identify and monitor acoustic energy that the valve 106 generates as well as other noise that, as noted above, can distort the data of the signals from the valve 106. This distortion can obfuscate issues with the valve that would normally be readily apparent from observation of certain changes in the acoustic waves. The processing component 114 can process the data from the signals to form an energy signature for the valve 106. The energy signature comprises data that is effectively free of the effects of acoustic energy that does not emanate from the valve 106. In one example, comparing the data of the energy signature with a known spectra of energy that is consistent with problematic operation can help identify and/or predict issues with the valve 106. As a result, the valve 106 can undergo pre-emptive and/or timely maintenance to mitigate damage with the valve 106 and/or potential problems, e.g., with the process and/or process facility.

Figure 2:
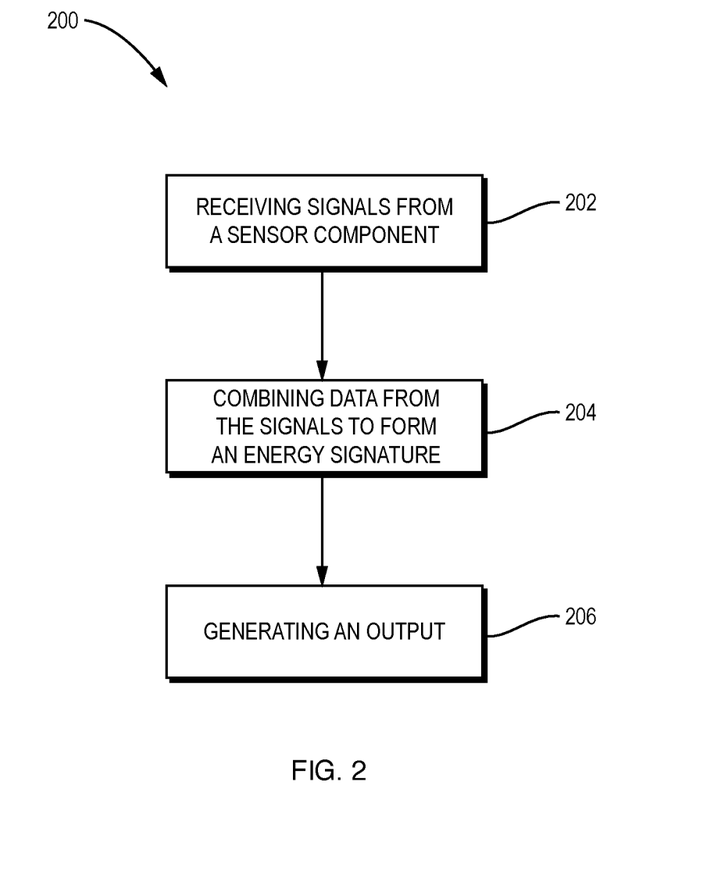
FIG. 2 depicts a flow diagram of an exemplary embodiment of a method for processing signals to remove and/or filter acoustic energy from the signals.

FIG. 2 depicts a flow diagram for an exemplary embodiment of a method 200 for processing data from signals to remove and/or filter noise. The method 200 includes, at step 202, receiving signals from a sensor component, at step 204, combining data from the signals to form an energy signature for the valve, and, at step 206, generating an output comprising data manifesting the energy signature.

Figure 3:
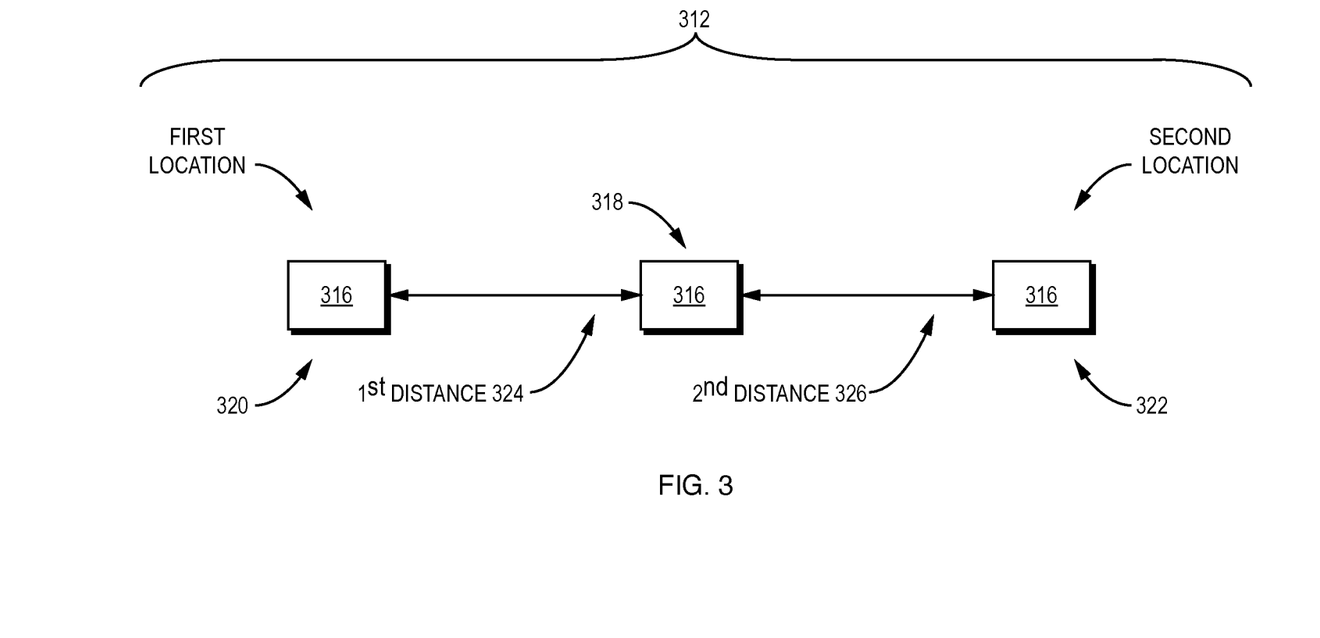
FIG. 3 depicts a schematic diagram of an exemplary configuration of a sensor component with sensors that can measure acoustic energy at a valve.

The step of receiving signals (e.g., at step 202) may utilize a plurality of sensor elements distributed in proximity to the valve. FIG. 3 illustrates one configuration for the sensor component 312 that includes one or more sensor elements 316 disposed in at least two locations (e.g., a first location 318, a second location 320, and a third location 322). The sensor 316 at the first location 318 resides proximate the valve (e.g., valve 106 of FIG. 1). The sensor 316 at the second location 320 and third location 322 are spaced apart a distance (e.g., a first distance 324 and a second distance 326) relative to the first location 318. In one example, the first distance 324 and the second distance 326 position the sensors 316 at the second location 320 and the third location 322 approximately the same distance from the sensor 316 at the first location 318.

The step of combining data from the signals to form an energy signature (e.g., at step 204) manipulates the data of the signals from the sensor elements 316. This data can include, in one example, data from a first signal from the sensor 316 at the first location 318. The data can also include data from a second signal and a third signal from the sensor 316 found at, respectively, the second location 320 and the third location 322.

During processing, the method 200 can sample the data from the signals according to a sampling pattern. Examples of the sampling pattern can implement a time delay that accounts for propagation of acoustic waves over the distance that separates the locations 318, 320, 322. In one implementation, the time delay includes a first delay, which the method 200 uses to obtain a first sample and a second sample from the data of the first signal. The time delay can also include a second delay and a third delay that the method 200 uses to obtain a third sample and a fourth sample from, respectively, the second signal and the third signal. In one example, the second delay is the same as the third delay. The value for the time delay (e.g., the first delay, the second delay, and the third delay) can include a fixed delay value. Examples of the fixed delay value can measure a travel time of sound between the first location 318 and the second location 320 and/or the first location 318 and the third location 322, as desired.

The step of generating an output (e.g., at step 206) can incorporate data that manifests the value of the energy signature. Examples of the output can be configured for display on a screen, e.g., for observation by a technician. In one embodiment, the method 200 may include one or more steps for comparing the spectrum of the energy signature to a threshold criteria and/or other quantitative measure. Examples of the threshold criteria can include one or more spectrum of energy that indicate the valve is operating correctly and/or improperly. Implementation of these steps can help diagnose problems with the valve. For example, changes in the spectrum of the energy signature that satisfy the threshold criteria (e.g., is above the identified spectrum, is equal to the identified spectrum, and/or is less than the identified spectrum), can indicate problems with the valve (e.g., leaks, cavitation, and/or other problems). Utilizing the filtering schemes to remove noise from data that identifies problems with the valve, as contemplated herein, can ensure that any changes in the spectrum comport with operation of the valve, and are not distorted by noise generated elsewhere.

Figure 4:
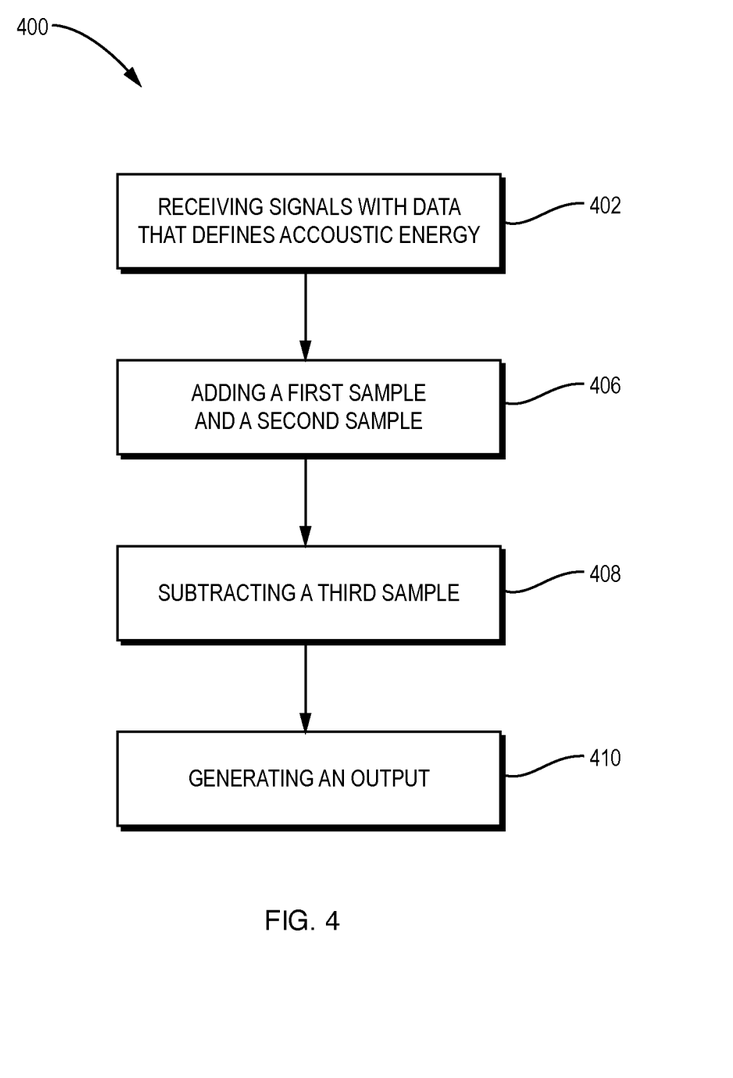
FIG. 4 depicts a flow diagram of an exemplary embodiment of a method for filtering noise from signals that identify acoustic energy at a valve.

FIG. 4 depicts a flow diagram of another exemplary embodiment of a method 400 to generate an energy signature that manifests acoustic energy at a valve. The method 400 includes, at step 402, receiving signals with data that defines acoustic energy. The method 400 also includes, at step 406, adding a first sample of data from a first signal and a second sample of data from the first signal to form a first preliminary sample and, at step 408, subtracting a third sample of data from a second signal from the first preliminary sample to form an energy signature. The method 400 also includes, at step 410, generating an output with data that manifests the energy signature.

Figure 5:
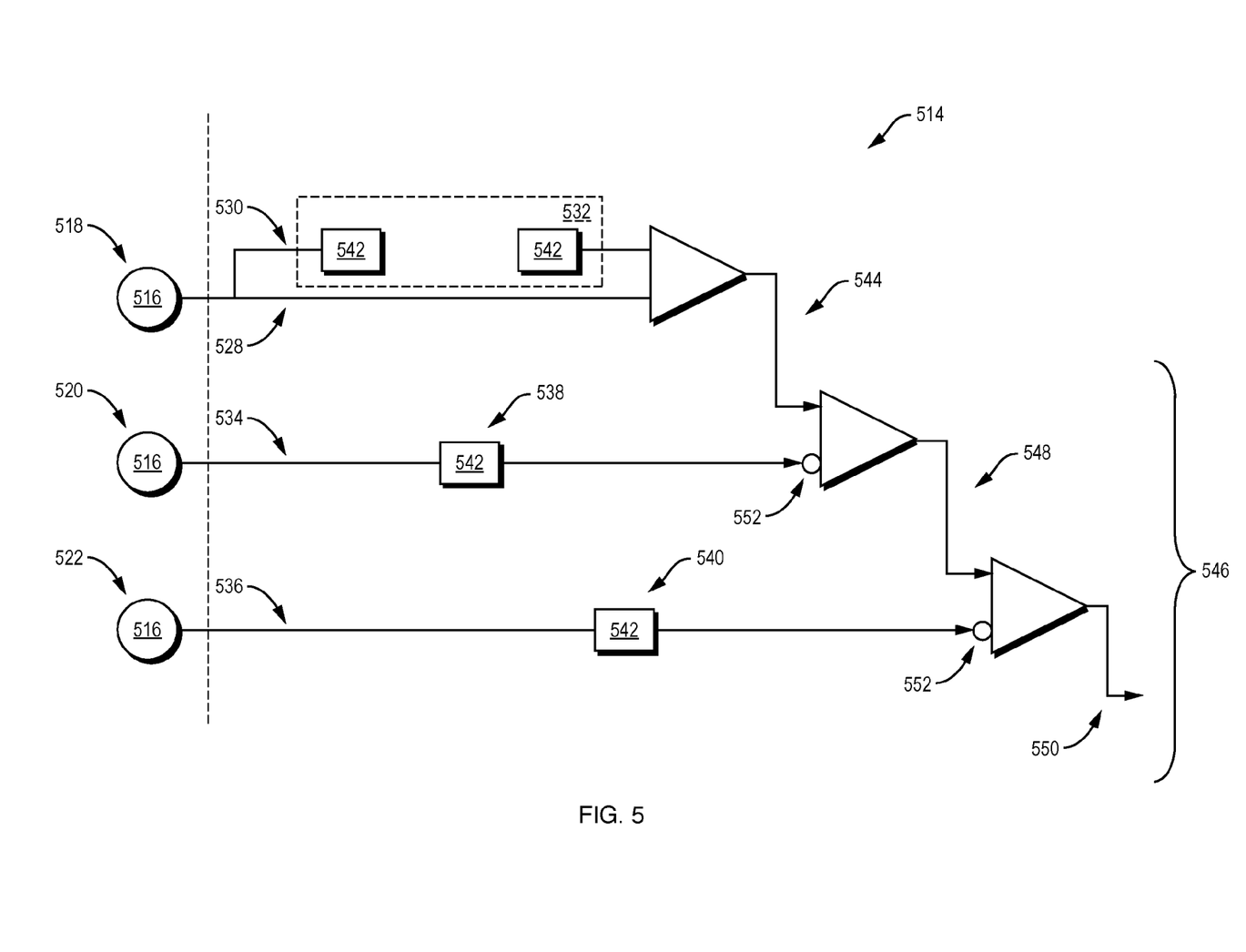
FIG. 5 depicts a schematic diagram of an exemplary configuration of a processing component that can process signals to remove and/or filter acoustic energy from the signals.

The steps of the method 400 are useful to free the energy signature of acoustic noise from upstream and downstream of the valve. The schematic diagram of FIG. 5 illustrates one exemplary configuration of the processing component 514 that can execute the addition and subtraction steps. As shown in the diagram, the sensor 516 at the first location 518 generates a first sample 528 from a first signal. The processing component 514 can utilize the first sample 528 to generate a second sample 530, which includes a first delay 532. The sensor 516 at the second location 520 and the third location 522 generate, respectively, a third sample 534 and a fourth sample 536. The processing component 514 can further include a second delay 538 and a third delay 540 in, respectively, that define the sample time of third sample 534 and the fourth sample 536. In one embodiment, the first delay, the second delay, and the third delay may include one or more fixed delay values 542.

Further in FIG. 5, the step of adding (e.g., at step 406) combines data of the first sample 528 with the second sample 530 to form a first preliminary sample 544. The step of subtracting (e.g., at step 408) combines the first preliminary sample 544 with one or more other samples (e.g., the third sample 534 and the fourth sample 536) to form the energy signature 546. In the present example, the energy signature 546 includes a first energy signature 548 and a second energy signature 550. The energy signatures 548, 550 correspond to steps of subtracting the third sample 534 from the first preliminary sample 544 (to form the first energy signature 548) and to steps of subtracting the fourth sample 538 from the first energy signature 548 (to form the second energy signature 550). In one example, before subtraction occurs, the processing component 514 inverts the third sample 534 and the fourth sample 536, as generally noted at the numeral 552.

The steps of the method 400, and the configuration shown in FIG. 5, address propagation of acoustic noise that arises from the valve as well as from elsewhere along a pipe that connects to the valve. Noise from the valve propagates from the valve in both directions (e.g., to the upstream side and to the downstream side). Moreover, noise from elsewhere along the pipe propagates to the valve and, possibly, onto the other side of the valve.

In one example, the method 400 defines a sampling pattern for the data from the various signals, e.g., from the first location, the second location, and the third location. This sampling pattern may reflect a series of samples that are evenly spaced over time. Equations (1), (2), and (3) below are useful to model the propagation of the acoustic waves and this sampling pattern:

$$SV_i = N1_{i-1} + NV_i + N2_{i-1},\qquad \text{Equation (1)}$$

$$S1_i = N1_i + NV_{i-1} + N2_{i-2},\qquad \text{Equation (2)}$$

$$S2_i = N1_{i-2} + NV_{i-1} + N2_i,\qquad \text{Equation (3)}$$

where SV is the signal from the sensor at the first location, S1 is the signal from the sensor at the second location, S2 is the signal from the sensor at the third location, NV is the acoustic noise from the valve, N1 is the acoustic noise from the upstream side of the valve, N2 is the acoustic noise from the downstream side of the valve, i is the sample number, i−1 is the sample at a time one fixed delay value before the sample i, and i−2 is the sample two fixed delay values before the sample i.

Data from the signals SV, S1, and S2 can be combined to form the energy signature (SO), as follows in Equations (4), (5), and (6) below in which, $$SO_i = SV_i + SV_{i-2} - S1_{i-1} + S2_{i-1},\qquad \text{Equation (4)}$$

substituting for SV, S1, and S2 (as set forth in Equations (1), (2), and (3)) above into Equation (4) provides, $$SO_i = (N1_{i-1} + NV_i + N2_{i-1}) + (N1_{i-3} + NV_{i-2} + N2_{i-3}) - (N1_{i-1} + NV_{i-2} + N2_{i-3}) + (N1_{i-3} + NV_{i-2} + N2_{i-1}),\qquad \text{Equation (5)}$$

and reducing Equation (5) provides, $$SO_i = NV_i + NV_{i-2},\qquad \text{Equation (6)}$$

Figure 6:
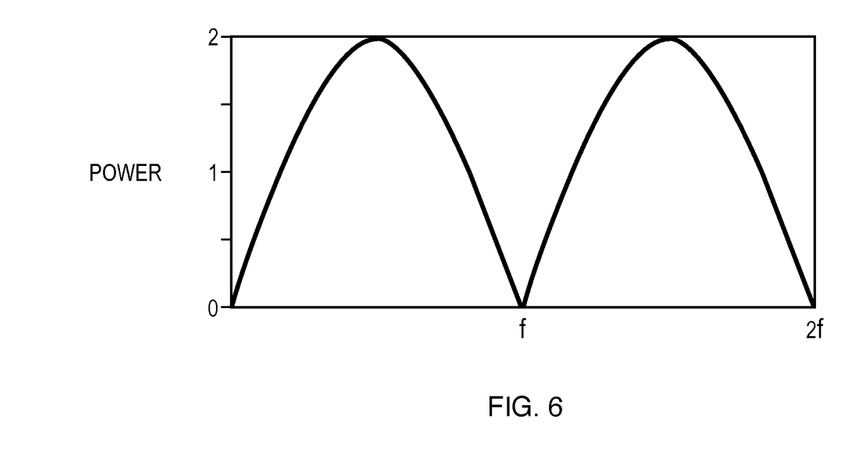
FIG. 6 depicts a plot of a power spectrum.

As shown in the forgoing equations, combining data from the first signal (e.g., the first sample 528) with data from a delayed version of the first signal (e.g., the second sample 530) effectively frees the data of the first preliminary sample 544 of acoustic noise that propagates from outside the valve. To this end, the value of the Equation (6) eliminates some frequencies and enhances other frequencies. For example, examining the Fourier transform of SO and letting t0 be the travel time from S1 to S2 yields:

$$T(f(t)-f(t-t0)) = F(w) - F(w)e^{-iwt0} = F(w)(1-e^{-iwt0}),\qquad \text{Equation (7)}$$

which shows that the spectrum of the signal F(w) is filtered by $(1-e^{-iwt0})$, where w is frequency. FIG. 6 depicts a plot of a power spectrum for Equation (7). This plot indicates that the proposed scheme will filter frequencies of 1/t0 and enhance frequencies of 1/(2t0). Thus, spacing of the locations of the sensors determine the frequency band that can be used for detection.

Figure 7:
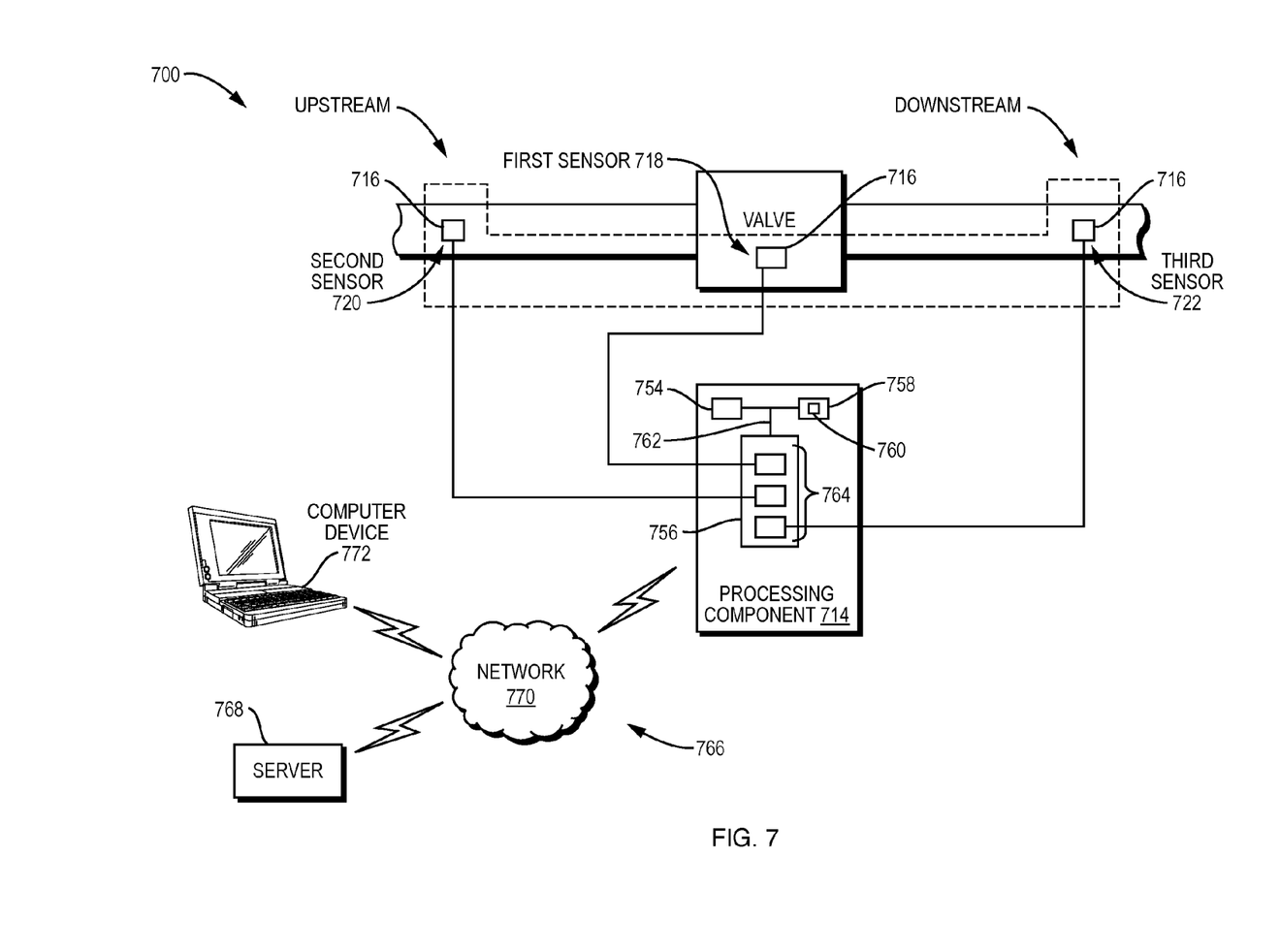
FIG. 7 depicts a schematic diagram of an exemplary embodiment of a system to monitor acoustic energy at a valve in a portion of a process facility.

FIG. 7 illustrates a schematic diagram of an exemplary embodiment of a system 700. The processing component 714 has a processor 754, control circuitry 756, memory 758, which can store one or more executable instructions 760, e.g., in the form of software and firmware that are configured to be executed by a processor (e.g., the processor 754). The processing component 714 can also includes busses 762 to couple components (e.g., processor 754, control circuitry 756, and memory 758) of the processing component 714 together. The busses 762 permit the exchange of signals, data, and information from one component of the processing device 714 to another. The control circuitry 756 can include sensor circuitry 764 that couples with the sensor elements 716 are the various locations 718, 720, 722.

Examples of the processing component 714 may communicate with a network system 766 with one or more external servers (e.g., external server 768) and a network 770 that connects the processing component 714 to the external server 768. This disclosure also contemplates configurations in which one or more programs and/or executable instructions (e.g., executable instructions 760) are found on the external server 768. The processing component 714 can access these remotely stored items to perform one or more functions disclosed herein. In one embodiment, a computing device 772 may communicate with one or more of the processing components 714 and the network 770, e.g., to interface and/or interact with the processing component 714 and/or other components of the system 700, as desired As set forth herein, the steps of the methods (e.g., method 200 of FIG. 2 and method 400 of FIG. 4) can embody one or more executable instructions, which can be coded, e.g., as part of hardware, firmware, software, software programs, etc. These executable instructions can be part of a computer-implemented method and/or program, which can be executed by a processor (e.g., processor 754 of FIG. 7) and/or a processing component (e.g., processing component 114, 214 of FIGS. 1 and 7).

Embodiments of the various control and processing devices (e.g., processing component 114, 714 of FIGS. 1 and 7) can comprise computers and computing devices with processors and memory that can store and execute certain executable instructions, software programs, and the like. These control devices can be a separate unit, e.g., part of equipment that control valves and other components in a process facility. In other examples, these control devices integrate with the valve, e.g., as part of the hardware (e.g., the valve positioner) and/or software configured on such hardware. In still other examples, these control devices can be located remote from the valve, e.g., in a separate location where the control device can receive information from sensors, issue commands and instructions using wireless and wired communication via a network (e.g., network 766 of FIG. 7).

These control devices may have constructive components that can communicate amongst themselves and/or with other circuits (and/or devices), which execute high-level logic functions, algorithms, as well as executable instructions (e.g., firmware instructions, software instructions, software programs, etc.). Exemplary circuits of this type include discrete elements such as resistors, transistors, diodes, switches, and capacitors. Examples of a processor (e.g., processor 754 of FIG. 7) include microprocessors and other logic devices such as field programmable gate arrays ("FPGAs"), ARM microcontroller, and application specific integrated circuits ("ASICs"). Although all of the discrete elements, circuits, and devices function individually in a manner that is generally understood by those artisans that have ordinary skill in the electrical arts, it is their combination and integration into functional electrical groups and circuits that generally provide for the concepts that are disclosed and described herein. In one embodiment, the processing devices (e.g., processing component 114, 714 of FIGS. 1 and 7) comprises analog circuitry and devices.

The structure of these control devices can permit certain determinations as to selected configuration and desired operating characteristics that an end user might convey via the graphical user interface or that are retrieved or need to be retrieved by the device. For example, the electrical circuits of these control devices can physically manifest theoretical analysis and logical operations and/or can replicate in physical form an algorithm, a comparative analysis, and/or a decisional logic tree, each of which operates to assign the output and/or a value to the output that correctly reflects one or more of the nature, content, and origin of the changes in parameters (e.g., flow parameters of a working fluid) that are reflected by the inputs to these control devices as provided by the corresponding control circuitry (e.g., control circuitry 756 of FIG. 7).

In one embodiment, a processor (e.g., processor 754 of FIG. 7) can also include state machine circuitry or other suitable components capable of controlling operation of the components as described herein. The memory (e.g., memory 758 of FIG. 7) includes volatile and non-volatile memory and can store executable instructions in the form of and/or including software (or firmware) instructions and configuration settings. Each of the control circuitry (e.g., control circuitry 756 of FIG. 7) can embody stand-alone devices such as solid-state devices. Examples of these devices can mount to substrates such as printed-circuit boards and semiconductors, which can accommodate various components including a processor, memory, and other related circuitry to facilitate operation, e.g., of processing component 114, 714 of FIGS. 1 and 7.

However, although processor, memory, and the components of control circuitry might include discrete circuitry and combinations of discrete components, this need not be the case. For example, one or more of these components can comprise a single integrated circuit (IC) or other component. As another example, a processor can include internal program memory such as RAM and/or ROM. Similarly, any one or more of functions of these components can be distributed across additional components (e.g., multiple processors or other components).

Moreover, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. Examples of a computer readable storage medium include an electronic, magnetic, electromagnetic, and/or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A non-transitory computer readable signal medium may include a propagated data signal with computer readable program code embodied therein, for example, in baseband or as part of a carrier wave. Such a propagated signal may take any of a variety of forms and any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language and conventional procedural programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for monitoring operation of a valve, comprising:
   a sensor component comprising:
      a first sensor;
      a second sensor; and
   a processing component that couples with the sensor component, the processing component comprising a processor, memory, and executable instructions stored in the memory and configured to be executed by the processor, the executable instructions comprising instructions for,
      receiving signals from the first sensor and the second sensor, the signals comprising data that corresponds with energy manifest from a valve and a pipe,
      sampling the data from the signals to create data samples, the data samples comprising a first sample, a second sample, and a third sample, the first sample and the second sample from a first signal that is expected to originate from the first sensor disposed at a first location proximate the valve, the third sample from a second signal that is expected to originate from the second sensor disposed at a second location on the pipe that is spaced apart from the first location proximate the valve, wherein the second sample comprises a first delay and the third sample comprises a second delay that is different from the first delay, and wherein the first delay and the second delay have values that account for propagation of acoustic waves over a distance that separates the first location from the second location,
      combining the data samples to form an energy signature for the valve by adding the first sample and the second sample to form a first preliminary sample and subtracting the third sample from the first preliminary sample,
      comparing the energy signature to a threshold criteria defining a known spectra of energy that corresponds with problematic operation of the valve; and
      generating an output comprising data in response to the energy signature satisfying the threshold criteria so as to initiate maintenance that pre-empts damage due to the problematic operation of the valve.

2. The system of claim 1, wherein the first delay and the second delay comprise a fixed delay value that utilizes a travel time of sound from the first location to the second location.

3. The system of claim 2, wherein the first delay is two times the fixed delay value.

4. The system of claim 3, wherein the second delay has a value that is substantially equal to the fixed delay value.

5. The system of claim 1, further comprising
   a third sensor,
   wherein the executable instructions comprise instructions for,
      sampling data from a third signal that arises from the third sensor disposed at a third location that is spaced apart from the first location and the second location to create a fourth sample, wherein the fourth sample comprises a third delay that is different from the first delay, and
      subtracting the fourth sample from the energy signature.

6. The system of claim 5, wherein the third delay is substantially the same as the second delay.

7. The system of claim 5, wherein the second location and the third location are located on, respectively, an upstream side and a downstream side of the valve.

8. The system of claim 5, wherein the second location and the third location are equally spaced from the first location.

9. The system of claim 1, wherein the first sensor and the second sensor comprise a plurality of accelerometers.

10. The system of claim 1, wherein the first sensor and the second sensor comprise a plurality of pressure sensors.

11. The system of claim 1, further comprising a control valve having a positioner with integrated circuitry that integrates one or more of the processor, memory, and executable instructions therein, wherein the first location is on the control valve.

12. A device for monitoring noise emanating from a valve, comprising
   a processor;
   memory coupled with the processor; and executable instructions stored on the memory and configured to be executed by the processor, the executable instructions comprising instructions for,
receiving signals with data that defines acoustic energy that manifests from a valve and a pipe;
sampling data from the signals to create data samples, the data samples comprising a first sample, a second sample, and a third sample, wherein the second sample comprises a first delay relative to the first sample and the third sample comprises a second delay that is different from the first delay,
combining the data samples to form an energy signature for the valve by,
adding the first sample and the second sample of data to form a first preliminary sample;
subtracting the third sample of data from the first preliminary sample;
comparing the energy signature to a threshold criteria defining a known spectra of energy that corresponds with problematic operation of the valve; and
generating an output comprising data in response to the energy signature satisfying the threshold criteria so as to initiate maintenance that pre-empts damage due to the problematic operation of the valve,
wherein the first sample and the second sample comprise data from a first sensor at a first location proximate the valve,
wherein the third sample comprises data from a second sensor at a second location on the pipe that is spaced apart from the first location, and
wherein the first delay and the second delay have values that account for propagation of acoustic waves over a distance that separates the first location from the second location.

13. The device of claim 12, wherein the data measures acceleration.

14. The device of claim 12, wherein the second location is space apart from the first location a distance calculated according to, $$d = \frac{v}{2f},$$

wherein d is the distance, v is the speed of sound through a media, and f is a cut-off frequency for the acoustic energy.

15. The device of claim 12, wherein the second location is on a downstream side of the valve.

16. The device of claim 12, wherein the second location is on an upstream side of the valve.

17. The device of claim 12, further comprising subtracting a fourth sample of data from the signals from the energy signature, wherein the fourth sample comprises a third delay relative to the first sample that is different from the first delay, and wherein the fourth sample comprises data from a third sensor at a third location that is different from the first location and downstream from the second location.

18. The device of claim 17, wherein the third delay is the same as the second delay.

19. The device of claim 17, wherein the first delay, the second delay, and the third delay include a fixed delay value, and wherein the fixed delay value measures a travel time of sound from the first location to either the second location or the third location.

20. The device of claim 19, wherein the first delay is equal to twice the fixed delay value.

* * * * *